United States Patent [19]

Joslin et al.

[11] 3,994,643
[45] Nov. 30, 1976

[54] APPARATUS FOR BANDING ELASTOMERIC GLOVES

[75] Inventors: Joel A. Joslin, Sunset Hills; Alan B. Ranford, Desperes; John C. Vogler, Manchester, all of Mo.

[73] Assignee: Sherwood Medical Industries Inc., St. Louis, Mo.

[22] Filed: Jan. 31, 1975

[21] Appl. No.: 546,176

[52] U.S. Cl. ............................... 425/110; 118/239; 118/308; 264/279; 425/393
[51] Int. Cl.² .......................................... B29C 13/00
[58] Field of Search .......... 118/239, 240, 258, 308, 118/319, 323, 324; 239/177, 184, 185; 264/259, 271, 279; 425/113, 114, 340, 383, 393, 403, 60, 110, 125, 129; 2/168

[56] References Cited
UNITED STATES PATENTS

| | | | |
|---|---|---|---|
| 2,344,905 | 3/1944 | Short | 118/323 UX |
| 2,753,593 | 7/1956 | Duff | 425/393 X |
| 2,779,055 | 1/1957 | Burger | 425/393 |
| 2,781,738 | 2/1957 | Paasche | 118/323 X |
| 3,548,453 | 12/1970 | Garis | 425/113 X |
| 3,852,826 | 12/1974 | Schindler | 2/168 |
| 3,865,525 | 2/1975 | Dunn | 425/60 |

*Primary Examiner*—Richard B. Lazarus
*Assistant Examiner*—Mark Rosenbaum
*Attorney, Agent, or Firm*—Stanley N. Garber; William R. O'Meara

[57] ABSTRACT

Apparatus for applying an elastic band around the cuff of an elastic glove which includes extruding a stripe of elastomeric material around the cuff of the glove while on a glove form and curing the stripe. A tray carrying a row of glove forms, each having a glove thereon, is stopped to position one of the forms at a band applying station. A mast having an extruder nozzle adjacent the cuff edge is moved circumferentially about the cuff in a generally elliptical path to avoid engagement with adjacent forms while allowing the forms to be closely spaced for economical manufacturing.

23 Claims, 15 Drawing Figures

APPARATUS FOR BANDING ELASTOMERIC GLOVES

BACKGROUND OF THE INVENTION

This invention relates to a method and apparatus for making elastic gloves and more particularly for making banded elastic gloves.

In certain types of elastic gloves, it is highly desirable to prevent the cuff portion from rolling downward from the edge to the palm or hand portion during use. For example, in surgical gloves it is important to provide a glove which will not roll. It is also important that the cuff is suitably tensioned to provide a relatively tight fit about the wrist or forearm of the surgeon. In U.S. Pat. No. 2,325,330, a band of elastic rubber stock is applied to the edge portion of the cuff to retard roll-down and provide a reinforcement at the edge. Gloves manufactured in accordance with this patent have cuff bands which differ in color in accordance with glove size to provide a visual indication of the size. However, the use of such bands generally entails the separate manufacture of the bands, such as by making tubing and cutting bands from it, and manual application of the bands to the gloves while the gloves are on glove forms. This method of manufacturing banded gloves is relatively expensive because of the relatively high labor time and costs involved. Also, good adhesion and accurate manual positioning of the band relative to the cuff edge are not always obtained.

In U.S. Pat. No. 3,852,826, surgical gloves are made with colored cuff bands for visual identification of glove size, the band also adding strength to the cuff. In this patent, the glove forms are dipped into a tank of coagulant and then into a tank of latex. The cuff of the glove on the form is then dipped into a second tank of latex to apply the band. The forms are dipped with the cuff down so that the carrier holding the glove forms is necessarily also dipped into the latex. This method results in considerable cleanup problems as well as in waste of material, particularly where a second coagulant dipping is employed between dipping steps.

SUMMARY OF THE INVENTION

It is therefore an object of the present invention to provide an improved apparatus for making a banded elastic glove which results in relatively economical manufacture, while reducing or avoiding the above-mentioned undesirable aspects.

In accordance with one feature of the present invention, a stripe of an elastomeric material is extruded onto the cuff of a glove and cured in situ. In accordance with another aspect, latex delivery means is moved about a glove form to apply a latex band on the cuff of the glove while on the form.

These and other objects and advantages of the present invention will become apparent from the following description and accompanying drawings.

DESCRIPTION OF THE PREFERRED EMBODIMENT

Figure 1:
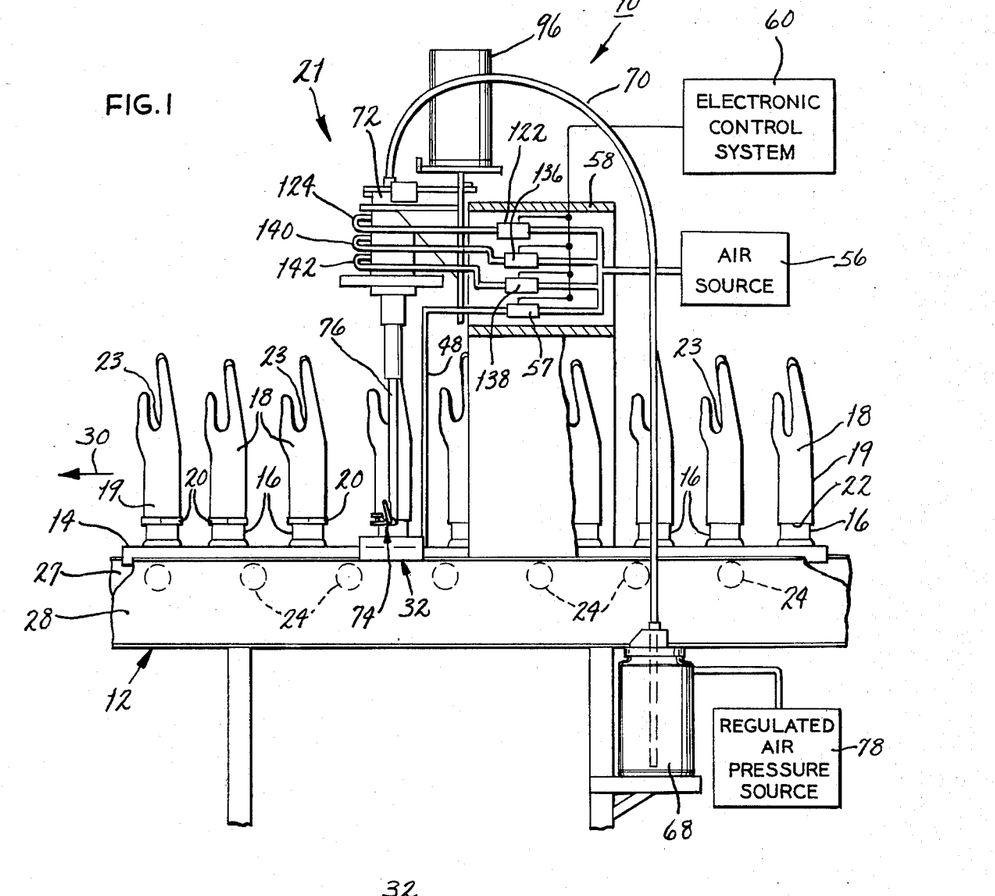
FIG. 1 is an elevational view of banding apparatus used in the method of making elastic gloves in accordance with the present invention.

Referring now to the drawings and particularly to FIG. 1, a glove banding apparatus 10 is shown mounted on a conveyor 12 which supports a tray or plate 14 carrying a row of spaced glove molds or forms 16 each having an elastic glove 18 formed thereon. As will be explained in detail hereinafter, the glove bander 10 applies a stripe or band 20 of elastomeric material onto the cuff 19 of each glove 18 at a banding station indicated generally at 21. The band 20 is preferably extruded onto the cuff and cured in situ to provide an elastic band tenaciously adhering to the cuff.

Gloves 18, which may be surgeons gloves, are preferably formed of latex although they may be formed of other elastomeric materials such as neoprene, vinyl chloride (plastisol), or other synthetic plastic material. The elastomeric material used to form the band 20, of course, is chosen such that it adheres to the material forming the body of the glove. The bands 20 are preferably formed also of latex.

The gloves 18 in the illustrated embodiment are preferably formed by the conventional dipping method. For example, the forms attached to tray 14 are first dipped, fingertips first, into a conventional coagulant, such as a calcium nitrate solution, removed from the coagulant, and allowed to dry. The coagulant coated forms are then dipped, fingertips first, into a quantity of liquid latex material and the forms are removed from the latex. The forms with the layer of latex may be subjected to a hot water leaching bath, for example, 180° F for about 10 minutes, to remove water solubles from the latex layer. The partially cured latex layers on the molds may then be fully curved in a heated oven, such as in a hot air oven at 220° F.

Such latex materials conventionally used include, in addition to natural latex, conventional stabilizers, thickeners, anti-oxidants, and vulcanizers or curing agents. The material used in banding the gloves is thickened sufficiently to obtain good extrusion characteristics. For example, the viscosity of the banding latex material may be between 22,000 and 28,000 cps.

The gloves 18 on the forms 16 in FIG. 1 are preferably only partially cured. In this way, the banding may be performed while the curing of the gloves takes place so as not to require additional time for banding. It has been found that the application of the latex banding material tenaciously adheres to the partially cured gloves. The gloves, of course, should be sufficiently cured at the time of banding to avoid damage to the material of the glove. After the gloves have been banded, as seen in FIG. 1 to the left of the banding apparatus 10, they are further processed in any suitable or conventional manner as previously mentioned herein to completely cure both the glove body and the latex material forming the band 20.

Figures 2, 3, 4, 5:
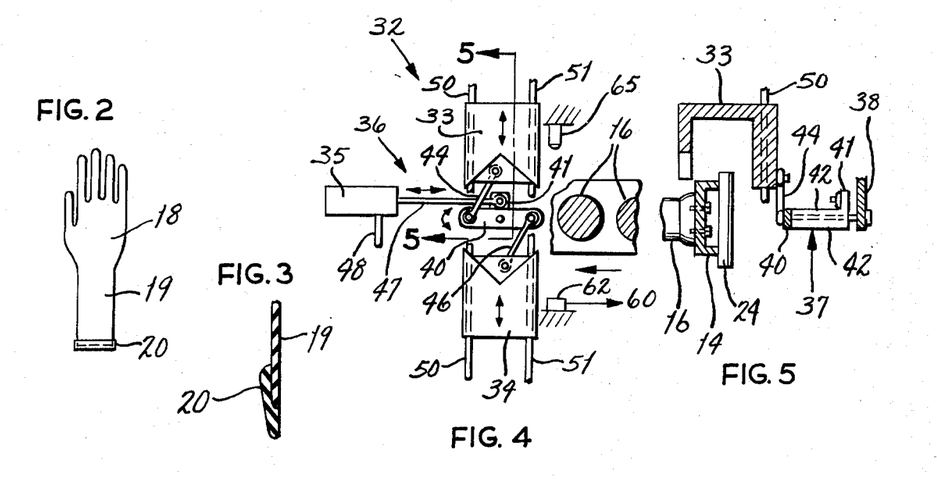
FIG. 2 is an elevational view of a finished elastic glove made according to the invention.
FIG. 3 is an enlarged fragmentary cross-sectional view of an edge portion of the finished glove of FIG. 2.
FIG. 4 is a plan view of a portion of the apparatus of FIG. 1 showing the glove positioning mechanism.
FIG. 5 is a cross-sectional view taken along the line 5—5 of FIG. 4.

The band 20 is applied to the marginal surfaces around the cuff adjacent the edge 22 and also preferably such that it extends downwardly beyond the edge 22 as is apparent in FIGS. 2 and 3. The band 20 retards roll-down of the cuff toward the palm or hand portion 23 of the glove when in use. It also increases the resiliency of the cuff so that it provides a tight fit around the wrist or forearm of the user as well as providing a reinforcement at the edge of the cuff to prevent tearing. A suitable dye may be added to the banding latex to make the band a different color than the glove, and a different color may be used for each size of glove to provide a visual indication of the glove size.

The conveyor 12 is comprised of a plurality of rollers 24 which support the tray 14 and which are rotated by any conventional or suitable drive means (not shown). The conveyor is provided with a pair of side rails 27 and 28 for guiding the tray 14 as the rollers move the tray forwardly in the direction of arrow 30.

A glove form positioning or stop mechanism indicated generally at 32 is mounted to the conveyor 12 for stopping each glove form 16 at the banding station 21. As seen in FIG. 4, the stop mechanism 32 includes a pair of opposed clamps 33 and 34 movable toward and away from each other and between which the tray and series of glove forms 16 pass. The clamps are actuated by an air cylinder 35 through a linkage 36 to move them simultaneously toward each other to clamp one of the glove forms accurately in position at station 21 for receiving a band 20. Linkage 36 includes an elongated lever or crank 37 mounted for rotation about its center on a stationary member 38, as seen in FIG. 5. Crank 37 has an upper lever 40 and lower drive lever 41 connected by a vertical post 42 with the lever 41 extending at an angle of 90° from the lengthwise axis of lever 40. A link 44 is pivotally connected at one end to one end of lever 40 and at the other end to the lower side of clamp 33. Also, a link 46 is pivotally connected at one end to the opposite end of lever 40 and the opposite end is pivotally connected to the lower side of clamp 34. A drive link 47 has one end connected to the piston of air cylinder 35 and the opposite end pivotally connected to the drive lever 41. Air cylinder 35 is biased, for example, by an internal spring to move link 47 in a rightward direction to move the clamps 33 and 34 apart while air pressure supplied by an air pressure line or conduit 48 causes the air cylinder 35 to move drive link 47 in a leftward direction to cause the clamps to move toward each other for clamping a glove form 16 between them. The clamping of a glove form 16 causes the entire tray 14 to stop but the rollers 24 continue to rotate under the tray. The clamps 33 and 34 are shown slidably mounted on a pair of stationary rods 50 and 51 which extend through bores in the lower portion of the clamp. The engaging face of each clamp is V-shaped to effect good centering of the form.

As seen in FIG. 1, the air pressure line 48 for controlling the air cylinder 35 is connected to receive air from an air pressure source 56 through an electrically operated air control valve 57 disposed in an upper portion of a supporting frame 58. The valve 57 is controlled by a signal from an electrical control system 60 to be described hereinafter. The air valve and hence the glove form positioning mechanism 32 are controlled in response to a signal from a glove form sensor, such as an infrared detector or sensor 62 in FIG. 4. An infrared source of light, indicated at 65, is positioned to provide light to detector 62. When a glove mold 16 comes between the source 65 and detector 62, a signal is supplied to the electronic control system which, in turn, operates air valve 57 to operate actuating cylinder 35 to clamp that glove form in position at station 21.

Figures 6, 7:
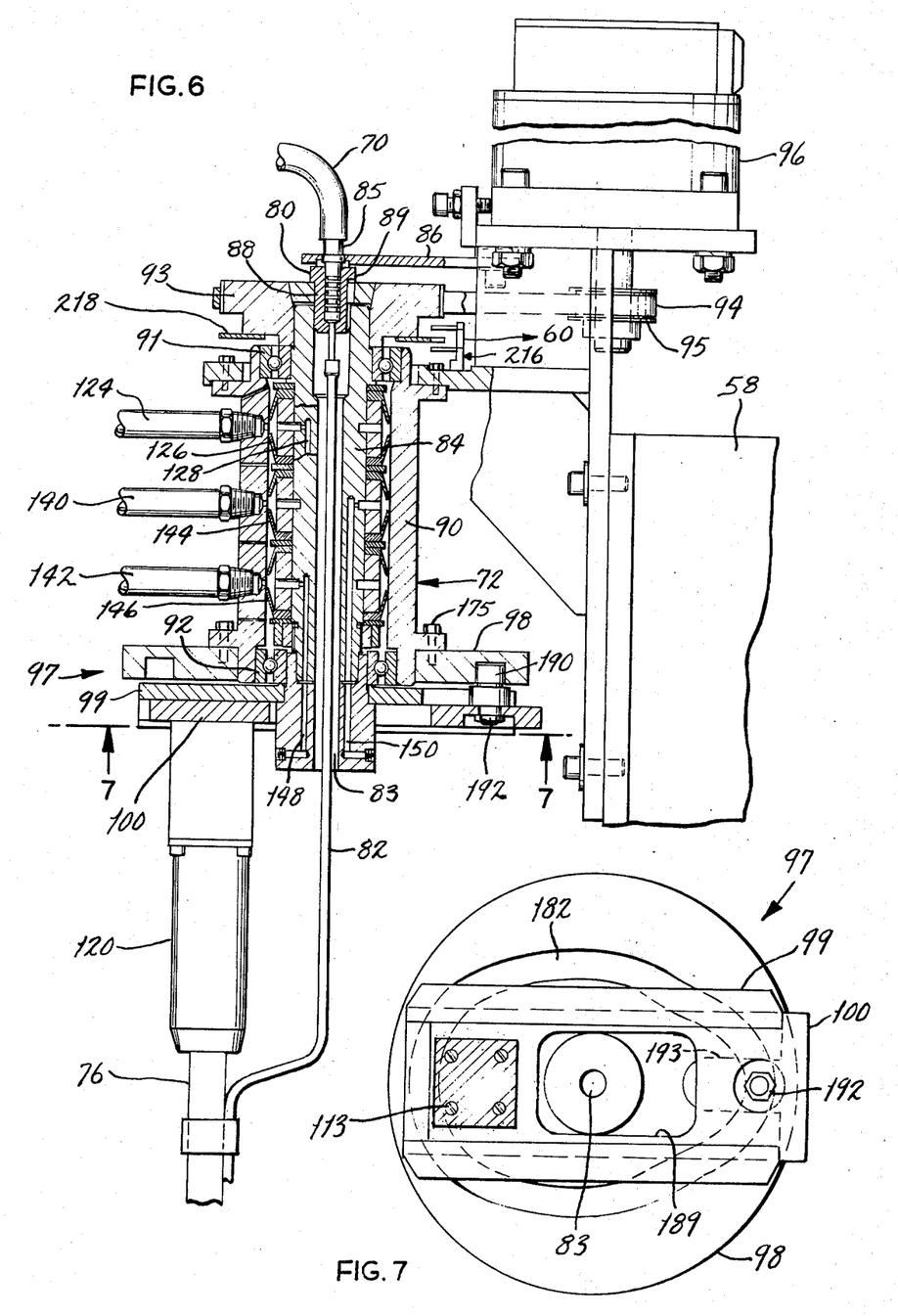
FIG. 6 is an elevational view partly in cross-section of a portion of the banding apparatus of FIG. 1 on a greatly enlarged scale.
FIG. 7 is a cross-sectional view taken along the line 7—7 of FIG. 6.
Figure 8:
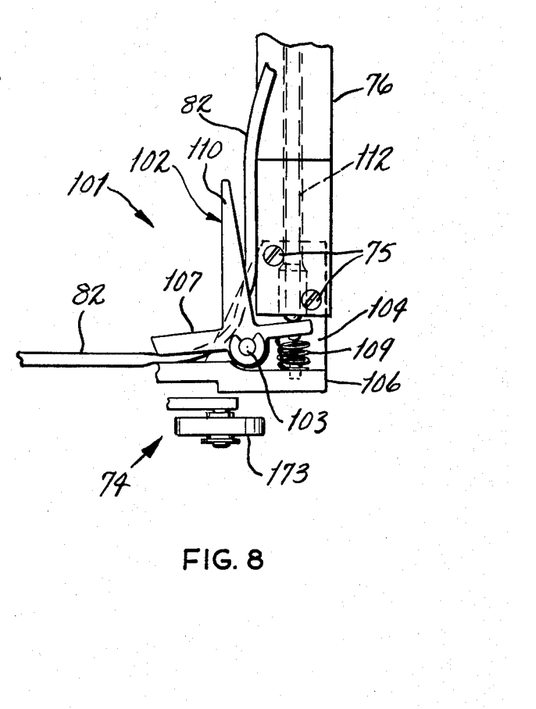
FIG. 8 is an enlarged fragmentary elevational view of an extruder nozzle mechanism at the lower end of the banding apparatus of FIG. 1.
Figure 9:
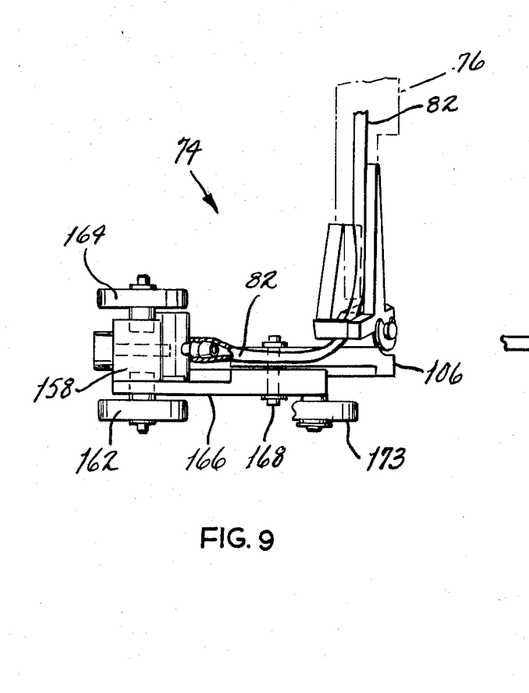
FIG. 9 is an enlarged side view of the extruder nozzle of FIG. 1.
Figure 10:
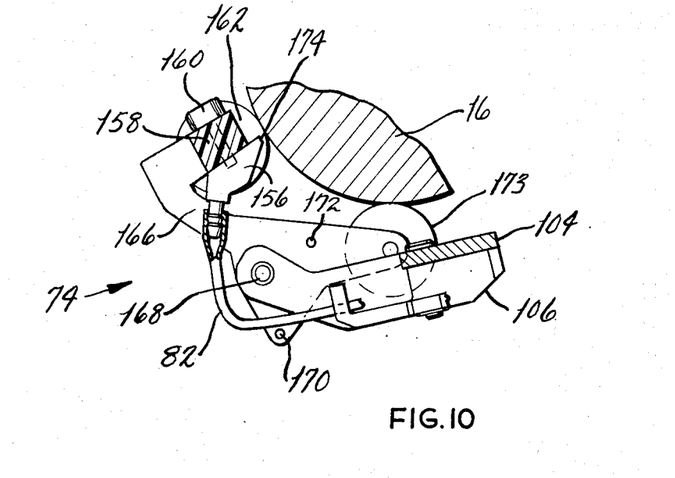
FIG. 10 is a top plan view, with parts broken away and in section of the nozzle mechanism of FIG. 9.

In FIG. 1, a container 68 of liquid latex material is supported on the conveyor 12 and connected by a fluid line or tube 70 to a head or fluid rotary seal 72 of bander 10. Liquid from line 70 is supplied to a latex applying device or extruder nozzle assembly indicated generally at 74 which extends generally radially from the mast and is connected, such as by screws 75, to the lower end of a movable mast 76 with the nozzle assembly extending radially from the mast. The mast 76 moves the extruder nozzle assembly 74 about the cuff of glove 18 to apply the band 20. A regulated air pressure source 78 is connected to pressurize the container 68. As seen in FIG. 6, the latex supply line 70 is connected through a fluid tight rotary seal 80 to a fluid line or tube 82 that extends downwardly through a bore 83 in a shaft 84 extending through the head 72, and along the mast 76 to the extruder nozzle assembly 74 as seen in FIGS. 8–10. The rotary seal 80 has an upper portion 85 connected by a supporting member 86 to the frame 58 in a manner to prevent its rotation. A lower portion 88 of the seal is fixed to the rotatable shaft 84 of the head such as by a spline connection. Annular seals 89 are engaged between the upper and lower portions of the rotary seal. The seal 80, of course, provides a fluid tight connection between lines 70 and 82 and allows line 82 to move relative to line 70 when shaft 84 rotates.

The shaft 84 is mounted for rotation in a stationary casing 90 of head 72 by bearings 91 and 92, and is driven by a pulley 93 fixed to the shaft, such as by a spline, that is driven by a belt 94. The belt 94 is disposed on a pulley 95 fixed to the shaft of a stepping motor 96 mounted on top of the conveyor frame. The lower end of the shaft 84 is coupled through a cam and pin assembly 97 to the mast 76 to move the mast and therefore the extruder nozzle assembly 74 about a glove on form 16 during a banding cycle. The assembly 97 includes a stationary cam member 98, a rotatable guide member 99 and a slide member 100 which will be described in greater detail hereinafter.

The flow of latex from the container 68 to the extruder nozzle assembly 74 is controlled by a pinch valve 101 disposed on the nozzle assembly 74, as best seen in FIGS. 8 and 9. Pinch valve 101 has a T-shaped movable valve member 102 pivotally connected by a pin 103 to a side wall 104 of a plate 106 of the nozzle assembly. The latex supply line 82 is positioned to extend between the left end of the horizontal portion 107 of the valve member 102 and the bottom wall of plate 106. A bias spring 109 is disposed between the right end of the portion 107 and the bottom wall of plate 106 to urge the right end upwardly and the left end downwardly to pinch the line 82 and prevent latex from flowing in the line. An upstanding portion 110 of valve member 102 may be used to manually release the line 82 for adjusting its position relative to the valve member. The line 82 is formed of a suitable material such as vinyl chloride tubing so that its passageway can be closed by the pinch valve 101 and opened by the resiliency of the tubing.

Figures 11, 12, 13, 14:
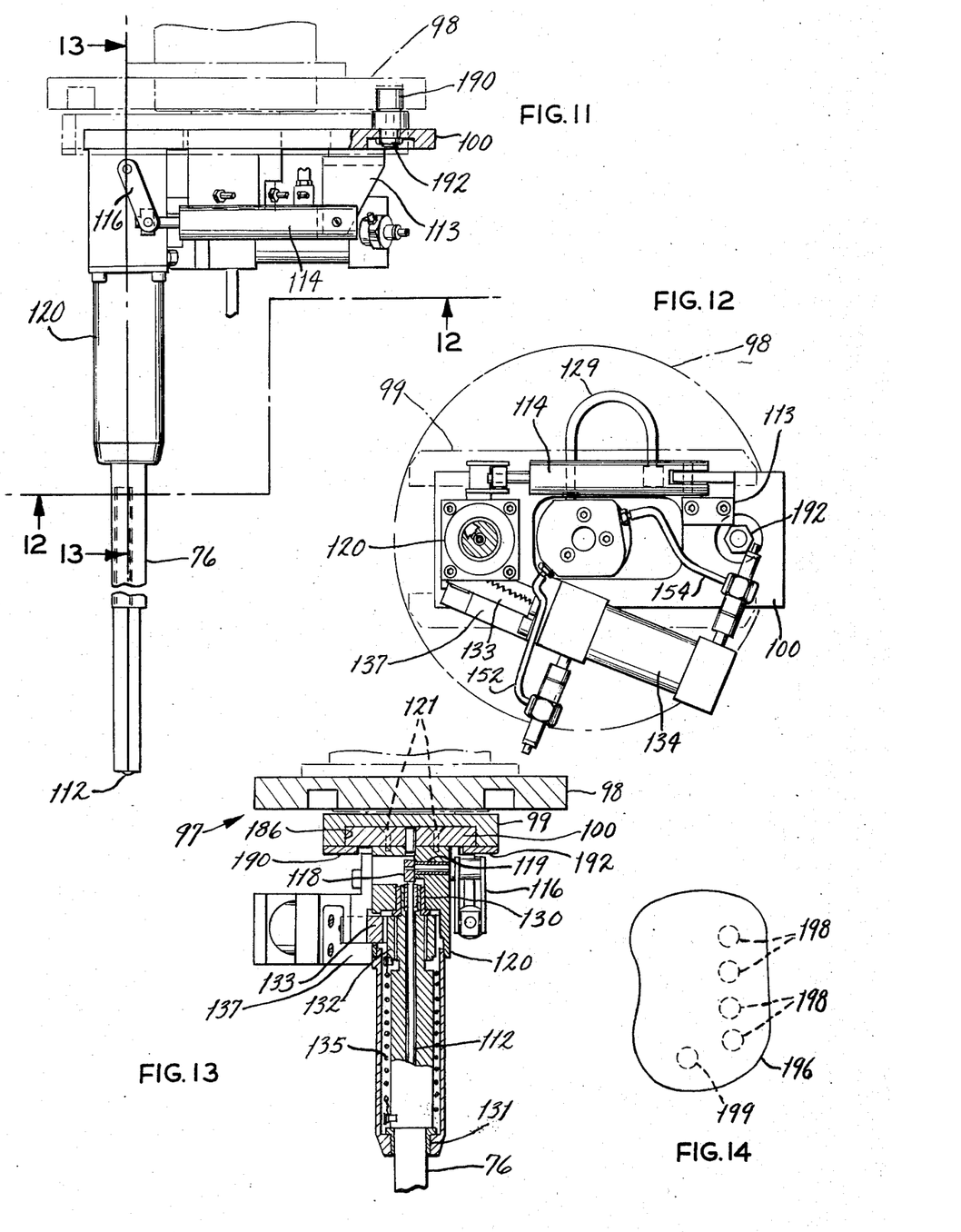
FIG. 11 is an elevational view of a portion of the banding apparatus of FIG. 1 greatly enlarged.
FIG. 12 is a view taken along the line 12—12 of FIG. 11.
FIG. 13 is a vertical cross-sectional view taken along the line 13—13 of FIG. 11.
FIG. 14 is a diagrammatic illustration showing the path of movement of the mast of the banding apparatus in FIG. 1 relative to the fingers of a glove form.

The pinch valve 101 is controlled by an actuating rod 112, as seen also in FIG. 13, which extends axially in a bore provided in the mast 76, the rod extending from the upper portion of the mast to the valve member 102. As seen in FIG. 8, the lower end of the rod 112 engages the upper side of the right end of the horizontal portion 107 of the valve member. Thus, downward movement of rod 112 moves the right end of the horizontal portion 107 of the valve downwardly against the force of spring 109 to release the line 82 and permit latex to flow through it.

The actuating rod 112 is controlled by an air cylinder 114 mounted under the head 72 by a bracket 113 to the slide member 100, such as by screws, as seen in FIGS. 11 and 12. The air cylinder 114 is connected by a pivotal link 116 to a cam 118 within a mast housing 120 which supports the mast 76 and which is connected by screws 121 to the slide member 100, as seen in FIG. 13. A pin 119 extends through the side wall of the mast housing 120 and interconnects the cam 118 and link 116 so that pivotal movement of the link effects rotational movement of pin 119 and cam 118. The cam engages the upper end of the actuating rod 112 so that when the link 116 is in an unactuated condition, for example, in the condition shown in FIG. 11, the rod 112 is in the upward position and the valve is pinching the line 82 as seen in FIG. 8 to close the valve or line and prevent latex flow. Upon actuation of the link 116 by the air cylinder 114, the cam 118 moves the rod 112 downwardly to the position indicated in FIG. 13 with the rod effecting the opening of the pinch valve 101 which allows latex to flow in the line. The cylinder 114 is normally biased to the unactuated condition (pinch valve open) by a spring within the cylinder.

Air cylinder 114 is supplied air from source 56 through a control valve 122 in the upper portion of frame 58 (FIG. 1) which, in turn, is controlled by electronic control system 60. A fluid line or tube 124 connects valve 122 to a rotating seal 126 in head 72 as seen in FIG. 6. The seal 126 is disposed on shaft 84 to connect the upper end of a passage 128 in shaft 84 in fluid communication with tube 124. A tube 129, as seen in FIG. 12, is connected between the lower end of passage 128 at the bottom end of shaft 84 and the acutating cylinder 114. Thus, the control valve 122 controls the pinch valve 101 (FIG. 8).

The mast 76 is rotated about its axis through a limited angular distance in order to move the nozzle assembly 74 between a position in which the nozzle is out of the path of glove forms 16 and a position in which the nozzle assembly is against a glove form for applying the stripe 20. In this way, the glove form does not hit the nozzle assembly when the glove form is moving into or out of position at the banding station. The mast 72 is mounted to housing 120 for limited rotation on its own axis relative to the housing by bearings 130 and 131, as seen in FIG. 13. This limited rotation of the mast is effected by a driven gear 132 (FIG. 13) fixed to the mast 76 and driven by a rack gear 133 which is also shown in FIG. 12. Rack 133 is moved in opposite directions by a conventional double acting or two-way air actuating cylinder 134. Gear 132 is coupled to the mast 76 by a torsion spring 135 connected at the top to the gear and at the bottom to the mast.

Acutating cylinder 134 is mounted to the mast housing 120 by a bracket 137, receives air from source 56 (FIG. 1) through a pair of control valves 136 and 138 connected respectively to tubes of air lines 140 and 142. As seen in FIG. 6, these tubes are connected through rotary air seals 144 and 146 respectively to passages 148 and 150 formed in shaft 84. The lower ends of the passages are connected by tubes 152 and 154 (FIG. 12) to the opposite ends of air pressure cylinder 134. Air pressure applied on one side of the cylinder piston (not shown) by tube 154 will move rack 133 leftwardly as viewed in FIG. 12 and, alternately, air pressure applied by the tube 152 will move the rack in the opposite direction. Thus, the control valves 136 and 138, which are operated by the electronic control system 60, control the position of the extruder nozzle assembly 74 for movement into and out of the path of movement of the glove forms during operation of the glove bander 10. In FIG. 10, the extruder and nozzle assembly 74 is shown in its position against a glove form 16 for movement around the form. When the mast is rotated to move the nozzle assembly 74 out of the path of a form 16, the mast rotates on its axis to move the assembly 74 arcuately about the mast axis away from form 16.

The nozzle assembly 74 has an extruder nozzle 156 secured to a supporting block 158 by a screw 160 with tube 82 connected to supply latex to the nozzle. A pair of wheels 162 and 164 are connected for rotation at the upper and lower ends respectively of the block 158. Supporting block 158 is fixed to a plate 166 pivotally connected to the plate 106 by a pin 168 and limited in movement by upstanding stop pins 170 and 172. A third wheel 173 is mounted for rotation at the right end of plate 166. The upper wheel 164 rides on the glove cuff 19 on form 16 while wheels 162 and 173 ride on the form below the cuff to maintain the extruder nozzle outlet orifice, indicated at 174, accurately spaced from the glove while moving around the form to apply a band of latex to the cuff.

In order to obtain high manufacturing efficiency, it is desirable or necessary to use glove forms which are mounted as closely together as practical so as to obtain a high rate of production. Glove bander 10 is capable of use with glove forms mounted relatively close together as seen in FIG. 1. This is accomplished in the illustrated embodiment by moving the mast 76 about each glove form 16 in a non-circular or generally elliptical path by means of the pin and cam assembly 97 so that it is able to pass between adjacent glove forms during each banding cycle without interference. The glove forms are mounted so that the plane of the palm of each is normal to the direction of movement of the forms.

As previously mentioned, the mast 76 is driven by motor 96 through shaft 84 and the pin and cam assembly 97. More particularly, the stationary cam member 98 of the assembly is mounted by bolts 175 to a flange at the lower end of housing 90 of the head 72 as best seen in FIG. 6. The camm has a generally elliptical cam groove 182 formed in the bottom face of the cam and related relative to the orientation of the glove forms 16 such that its longer axis is parallel to a line extending normal to the palms of the glove forms, as will be discussed hereinafter. The guide member 99 is fixed, such as by a spline (FIG. 6), to the shaft 84 below the cam member 98 for rotation with the shaft. As best seen in FIG. 13, guide member 99 has a slot 186 extending radially relative to the axis of shaft 84. Slot 186 is open at the bottom and at the opposite ends of the guide member. The slide member 100 is disposed in slot 186 for sliding radial movement relative to the guide member 99. A pair of lengthwise extending retaining plates 187 and 188 are connected, such as by screws, to the bottom of the guide member 99 which extend inwardly of the slot from the opposite sides and under the slide member 100 so as to maintain member 100 within the slot. The screws 121 connect the housing 120 of mast 76 to the slide adjacent to one end of the slide. A slot 189 in slide 100 allows shaft 84 to pass through it without interference.

As seen in FIGS. 6, 7, 11 and 12, a cam follower or pin 190 is fixed by a nut 192 to the slide member 100 adjacent the end opposite the end to which the mast housing 120 is connected. Pin 190 is shown as a conventional roller pin which extends upwardly from slide 100, through a slot 193 in guide member 99, and into the cam groove 182. In the illustrated embodiment, the rotation of the shaft 84 causes rotation of the guide member 99 which, in turn, causes rotation of slide 100. As slide 100 rotates, the pin 190 engages and follows the walls of cam groove 182 to cause the slide and mast 76 connected thereto to move in a non-circular path, the pin 190 effecting a radial component of movement as the mast moves around the glove form. The path that the mast 76 traverses as it moves around each glove form 16 during a banding cycle is generally elliptical and is indicated by the generally elliptical line or closed curve 196 in FIG. 14. The fingers of the glove form are indicated in phantom at 198 and a thumb at 199. It will be noted that the longer axis of the curve 196 is normal to the longer axis of the cam groove 182 in FIG. 7. This is because pin 190 is at the end of the slide 100 opposite the end to which the mast is connected. Also, because of the previously-mentioned orientation between the cam groove 182 and glove forms 16, the longer axis of the path of the mast or elliptical curve 196 is parallel to the width dimension of the hand portion of the glove form and row of fingers 198 as seen in FIG. 14. In this way, the mast is able to move between the closely spaced glove forms without interference, that is, without it engaging any part of the forms. Since the plate 166 carrying nozzle 156 is pivotal relative to the mast, the nozzle is maintained by the spring 135 and the mast closely adjacent the cuff for obtaining a good band even though the cuff is substantially circular.

Figure 15:
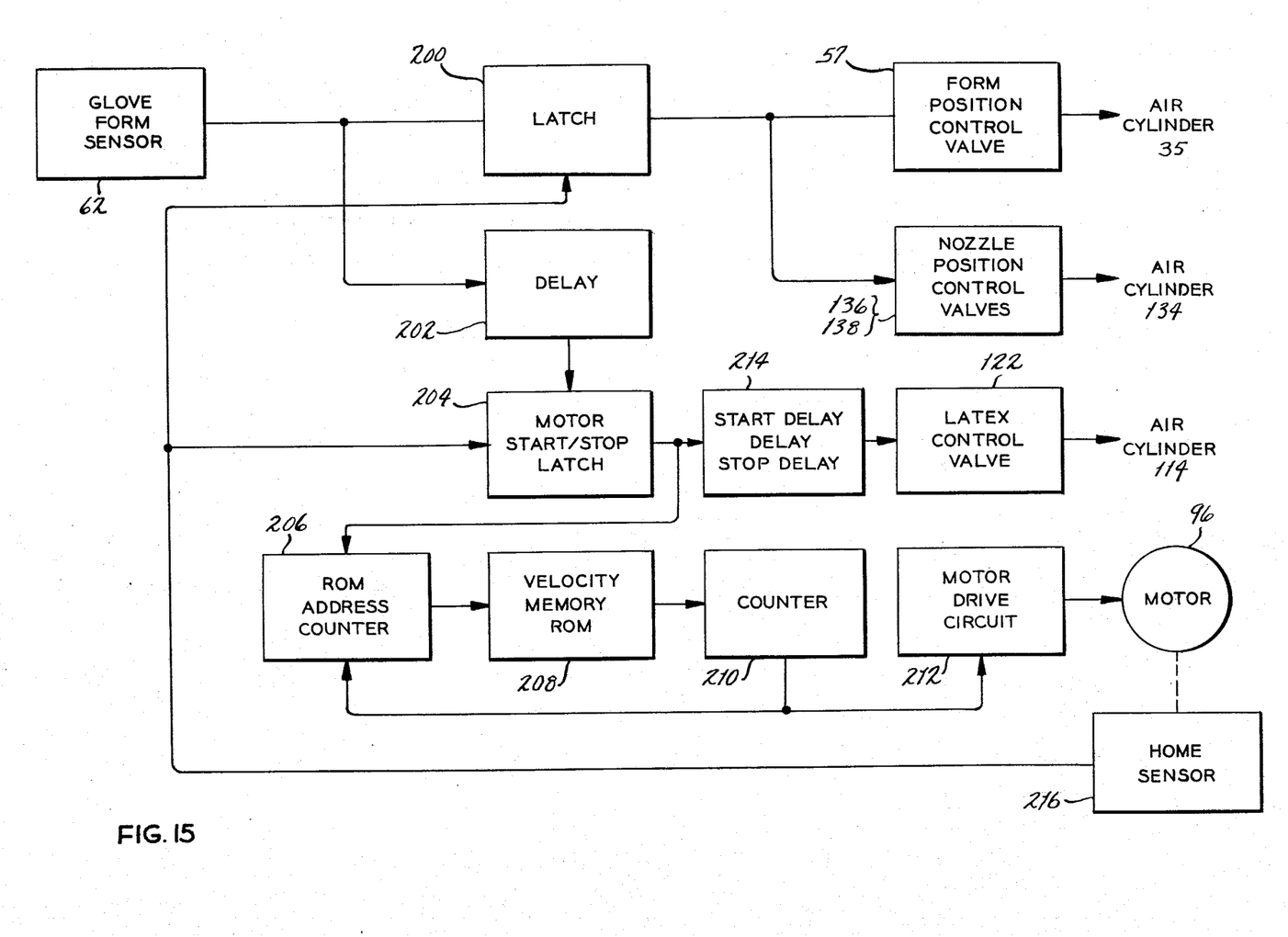
FIG. 15 is a block diagram of the control system for operating the banding apparatus of FIG. 1.

Control system 60 for automatically controlling the operation of banding apparatus 10 is shown in block diagram in FIG. 15. However, manual, semi-manual, or other automatic control systems may be employed to control apparatus 10 if desired.

As seen in FIG. 15, a signal from the glove form sensor 62 is applied to a glove form latch circuit 200 which actuates the form positioning air valve 57 to cause air cylinder 35 to actuate mechanism 32 for positioning the sensed glove form accurately at station 21. The nozzle position valve 136 is also actuated through latch 200 to actuate air cylinder 134 and move the extruder nozzle assembly 74 into its latex applying position against the glove form. The sensor 62 as connected in FIG. 15, also supplies a signal to a delay circuit indicated at 202 which, in turn, operates a motor start-stop latch 204. The delay circuit 202 allows time for the glove form to be accurately positioned at station 21 and the nozzle assembly 74 to be positioned before the motor start-stop latch 204 is capable of operating the latex pinch-off valve 101 and the motor 96. The output of the motor start-stop latch 204 is connected through a delay circuit 214 to operate control valve 122 which actuates air cylinder 114 which, in turn, opens pinch valve 101 after the motor 96 has started. The motor start-stop latch 204 is also shown connected to command a ROM address counter 206 to address a velocity memory or read only memory, ROM, 208 which, in turn, loads a number into a counter 210 that counts down. The down counter counts down and when it reaches zero, supplies a pulse to a motor drive circuit 212 which pulses the stepping motor 96, for example, 1.8°. At the same time, the pulse goes back to the ROM address counter 206 which advances that one count and which then goes to the loop to provide a new address for the ROM 208 which, in turn, loads a new count into the down counter 210. The clock or down counter counts back down to zero providing a new pulse to the motor drive circuit 212 to further drive the stepping motor and another clock pulse to the ROM address counter. This is continued until a complete banding cycle occurs, that is, until the mast has completely moved around the glove form and has applied a latex band 20.

A "home" sensor 216 is shown in FIG. 6 as including an infrared source and detector on opposite sides of a disc 218 connected to rotate with shaft 84. The disc has a slot that passes between the source and detector and which corresponds to the home position of the mast 76. The system can be operated or programmed so that the mast past the home position a predetermined amount where desired. This causes the start end of the band 20 to be slightly overlapped by the finish end of the band and thus ensures a completed band. When the mast has moved or almost moved the predetermined amount past the home position, the motor 96 is momentarily stopped, the control valve 122 operated to allow the closing of pinch valve 101 to stop the flow of latex, and the control valve 138 is actuated to actuate cylinder 134 in a direction to move the nozzle assembly 74 out of the path of the glove forms. The motor 96 is then reversed to move the mast 76 back to the home position. When reaching the home position, the home sensor 216 as seen in block form in FIG. 15, provides a reset signal to the start-stop latch 204 to stop the motor 96, and a signal to latch 200 to operate the control valve 57 which operates mechanism 32 in a direction to release the banded glove form. This allows the tray 14 to move and bring the next form into the banding station 21.

The ROM program which controls the velocity of the stepping motor 96 is used to maintain a substantially constant tangential velosity of the nozzle 156 relative to the glove form being banded even though the symmetry of the cam mast combination calls for a non-circular path. This is a preferred program where the flow of latex is maintained at a constant rate. In this way, the band 20 has a substantially constant thickness.

While preferred forms of the invention has been shown and described herein, it will be understood that various changes and modifications thereto may be made without departing from the spirit and scope of the invention.

What is claimed is:

1. A glove banding apparatus comprising support means, a plurality of glove forms connected to said support means in fixed relation with the longitudinal axes of said glove forms parallel to each other, each of said glove forms having finger, palm, and cuff portions, said glove forms being adapted to have an elastomeric material applied thereto to form gloves thereon with each glove having finger, palm, and cuff portions, and means for applying a band of elastomeric banding material around the cuff portion of at least some of said gloves comprising means operably associated with said support means for moving said support means to position one of said glove forms at a banding station, a mast at said banding station having its longitudinal axis extending generally, parallel to the longitudinal axes of said glove forms, a nozzle adjacent to one end of said mast and positionable adjacent the cuff portion of the glove on said one glove form, means operably associated with said mast for moving said mast in a path around said one glove form, and means connected in fluid communication with said nozzle for supplying liquid elastomeric banding material to said nozzle during said movement of said mast around said one glove form thereby applying a band of said liquid banding material around the cuff portion of the glove on said one glove form, said glove forms being closely spaced from each other in row formation such that said mast would engage a glove form next adjacent said one glove form if it moved along any circular path about said one glove form during the application of said band, said means for moving said mast including means, operatively associated with said mast for moving said mast along a noncircular path around said one glove form so as to avoid engagement with said next adjacent glove form.

2. The apparatus of claim 1 including means at said banding station for engaging and stopping said one glove form to thereby stop said support means for applying said band to the glove on said one glove form.

3. The apparatus of claim 1 wherein said elastomeric banding material comprises latex.

4. The apparatus of claim 1 wherein said mast is rotatable on its own longitudinal axis to position said nozzle into a band applying position and to move said nozzle radially outwardly away from said one glove form to permit movement of said support means so as to position another glove form at said banding station.

5. The apparatus of claim 4 including a plate member extending generally radially from said mast, said nozzle being connected to said plate member, a pair of wheels circumferentially spaced from each other and maintaining the nozzle predeterminately spaced from the glove on said one glove form during the application of the band thereto.

6. The apparatus of claim 5 wherein said plate member is pivotally connected to said mast to allow radial pivotal movement of said nozzle during movement thereof around said one glove form.

7. The apparatus of claim 1 wherein said mast moves around said glove form at least through 360° so that said band extends entirely around the cuff of the glove on said one glove form.

8. The apparatus of claim 1 wherein said means for supplying liquid elastomeric material to said nozzle includes flexible tube means connected in fluid communication with said nozzle, and pinch valve means for controllably closing said tube to control the flow of the liquid elastomeric material to said nozzle.

9. The apparatus of claim 1 wherein the finger portion of each of said glove form is above said support means, supporting means above said finger portion for supporting said mast, and the plane of each of the palms of the glove forms are substantially normal to the direction of movement of the glove forms.

10. The apparatus of claim 1 wherein said means for moving said mast includes rotatable drive means, and means coupling said drive means to said mast to move said mast about the glove form in said non-circular path.

11. The apparatus of claim 10 wherein said coupling means includes cam means and a cam follower engaged with said cam means to move said mast along a generally elliptical path about the glove form.

12. The apparatus of claim 11 wherein the longer axis of the generally elliptical path is parallel to the plane of the palm of each glove and normal to the longer axes of the fingers of each glove.

13. The apparatus of claim 12 wherein said coupling means includes a guide member connected to rotate with said drive means, and a slide member connected to said mast for moving said mast about said one glove form at said banding station, said cam follower being connected to said slide member, said slide member being slidably mounted to said guide member and rotated by said guide member, said slide member being slidable along a radial component of movement by said cam means and simultaneously rotated by said guide member to effect said elliptical path of movement of the said mast.

14. The apparatus of claim 13 wherein said mast is fixed to one end of said slide member and said cam follower is connected to the opposite end of said slide member.

15. The apparatus of claim 14 wherein said cam means is a member having a generally elliptical groove, and said cam follower is a pin extending into said groove.

16. The apparatus of claim 1 further comprising clamping means including a pair of clamps movable toward each other and the glove form to engage and hold the glove form stationary in position at said banding station, said pair of clamps being movable away from each other to permit the glove form to move away from the banding station after the band of elastomeric material has been applied to the cuff.

17. The apparatus of claim 1 including means for moving said nozzle at a substantially constant tangential velocity relative to the form when applying a band to the cuff.

18. A glove banding apparatus comprising support means, a plurality of glove forms supported on said support means in fixed relatively close relation with the longitudinal axes of said glove forms parallel to each other, each of said glove forms having finger, palm, and cuff portions, said glove forms being adapted to have an elastomeric material applied thereto to form gloves thereon with each glove having finger, palm, and cuff portions, and means for applying a band of elastomeric banding material around the cuff portion of at least some of said gloves comprising means operably associated with said support means for moving said support means to position one of said gloved forms at a banding station, a mast at said banding station having its longitudinal axis extending generally parallel to the longitudinal axes of said glove forms, means operably associated with said mast for moving said mast in a path around said one gloved form, a nozzle adjacent one end of said mast and positionable adjacent the cuff portion of the glove on said one gloved form and having an outlet for directing banding material to said cuff portion, means connected in fluid communication with said nozzle for supplying banding material to said nozzle during said movement of said mast around said one gloved form thereby applying a band of said banding material around the cuff portion of the glove on said one gloved form, plate means, means operably associated with said plate means connecting said nozzle to said mast, spacer means connected to said plate means and engaging said one gloved form at circumferentially spaced points on said one gloved form during the application of said band to maintain said nozzle outlet closely spaced from the cuff of the glove on said one gloved form during the application of said band, and pivotal connection means located circumferentially between said spaced points connecting said plate means with said mast and permitting pivotal movement of said plate means and nozzle in planes normal to the longitudinal axis of said gloved form.

19. The apparatus of claim 18 wherein said spacer means respectively comprise first and second circumferentially spaced wheels rotatable about axes parallel to the longitudinal axis of said one gloved form.

20. The apparatus of claim 19 wherein said spacer means further includes a third wheel coaxially connected with said first wheel with said first and third wheels on opposed sides of said nozzle outlet.

21. The apparatus of claim 18 wherein said means for moving said mast includes means for moving said mast to maintain a substantially constant tangential velosity of said nozzle relative to the glove on said one gloved form.

22. The apparatus of claim 19 including spring means urging said mast in a direction to move said wheels toward engagement with said one gloved form to position said nozzle for applying said band, and wherein said banding material supplying means includes a flexible tube coupled to said nozzle, and means controlling the flow of banding material through said tube.

23. A glove banding apparatus comprising support means, a plurality of glove forms connected to said support means in fixed relation with the longitudinal axes of said glove forms parallel to each other, each of said glove forms having finger, palm, and cuff portions, said glove forms being adapted to have an elastomeric material applied thereto to form gloves thereon with each glove having finger, palm, and cuff portions, and means for applying a band of elastomeric banding material around the cuff portion of at least some of said gloves comprising means operably associated with said support means for moving said support means to position one of said glove forms at a banding station, a mast at said banding station having its longitudinal axis extending generally parallel to the longitudinal axes of said glove forms, a nozzle adjacent to one end of said mast and positionable adjacent the cuff portion of the glove on said one glove form, means operably associated with said mast for moving said mast in a path around said one glove form, and means connected in fluid communication with said nozzle for supplying liquid elastomeric banding material to said nozzle during said movement of said mast around said one glove form thereby applying a band of said liquid banding material around the cuff portion of the glove on said one glove form, said mast being rotatable on its own longitudinal axis to position said nozzle into a band applying position and to move said nozzle radially outwardly away from said one glove form to permit movement of said support means so as to position another glove form at said banding station.

* * * * *